United States Patent [19]

Goldberg et al.

[11] Patent Number: 4,961,954

[45] Date of Patent: Oct. 9, 1990

[54] SURFACE MODIFIED SURGICAL INSTRUMENTS, DEVICES, IMPLANTS, CONTACT LENSES AND THE LIKE

[75] Inventors: Eugene P. Goldberg, Gainesville, Fla.; James W. Burns, Natick, Mass.; G. Sudesh Kumar, Maharastra, India; David C. Osborn, St. Louis, Mo.; Jeffrey A. Larson, Monrovia; John W. Sheets, Clearmont, both of Calif.; Ali Yahiaoui; Richard Robinson, both of Gainesville, Fla.

[73] Assignee: University of Florida, Gainesville, Fla.

[21] Appl. No.: 304,479

[22] Filed: Feb. 1, 1989

Related U.S. Application Data

[63] Continuation-in-part of Ser. No. 37,153, Apr. 10, 1987, Pat. No. 4,806,382.

[51] Int. Cl.$^5$ .......................... A01N 1/02; B05D 3/06
[52] U.S. Cl. .......................... 427/2; 427/36; 522/84; 522/85; 522/167; 604/96; 606/107; 623/1; 623/3; 623/66
[58] Field of Search ................ 427/2, 36; 522/84, 85, 522/167; 623/4, 5, 6, 1, 3, 66; 604/96; 606/107

[56] References Cited

U.S. PATENT DOCUMENTS 4,589,964 5/1986 Mayhan et al. .................. 522/85
4,806,382 2/1989 Goldberg et al. ................ 427/2

OTHER PUBLICATIONS

Knight, Patricia M. et al., *Surface Modification of Intraocular Lenses to Reduce Corneal Endothelial Damage,* Chemical Abstracts, vol. 92, 1980, p. 330; 203547f.

*Primary Examiner*—Michael Lusignan
*Attorney, Agent, or Firm*—Kerkam, Stowell, Kondracki & Clarke

[57] ABSTRACT

Improved medical devices and instruments prepared by an improved method of producing hydrophilic, gamma irradiation induced polymerized and chemically grafted coatings or plastic surfaces of articles adapted for contacting living tissue, the improvement comprising carrying out the graft polymerization in an aqueous solution under specific combinations of the following conditions:

(1) monomer concentration in the range of from about 0.5% to about 50%, by weight;
(2) total gamma dose in the range of from about 0.01 to less than about 0.50 Mrad;
(3) gamma dose rate in the range of from about 10 to about 2500 rads/min; and
(4) maintaining the molecular weight of the polymer in solution in the range of from about 250,000 to about 5,000,000.

13 Claims, No Drawings

SURFACE MODIFIED SURGICAL INSTRUMENTS, DEVICES, IMPLANTS, CONTACT LENSES AND THE LIKE

RELATED APPLICATIONS

The application is a continuation-in-part of application Ser. No. 037,153 filed Apr. 10, 1987, now U.S. Pat. No. 4,806,382, patented Feb. 21, 1989.

BACKGROUND OF THE INVENTION

1. Field of the Invention

The present invention relates to plastic surgical instruments, medical devices, prosthetic cardiovascular implants and implants for hard and soft tissue, contact lenses and the like, and methods for improving surfaces thereof.

2. Prior Art

Studies have shown that the surgical implantation of ocular implants such as intraocular lenses (IOL), etc., results in the loss of significant corneal endothelial tissue unless great care is taken to ensure a lack of contact between the device and the endothelium. Most ocular implants are constructed of hydrophobic polymethylmethacrylate (PMMA) polymers because of their superior optical qualities, resistance to biodegradation, etc. It has been found, however, that PMMA surfaces adhere to endothelial cells upon even casual contact and that separation of the surface therefrom results in a tearing away of the endothelial tissue adhered to the polymer surface. Similar adhesive interactions with other ocular tissues, i.e., the iris, can also cause adverse tissue damage. Other hydrophobic polymers which are used or have been proposed for use in ocular implants (i.e., polypropylene, polyvinylidene fluoride, polycarbonate, polysiloxane) also can adhere to ocular tissue and thereby promote tissue damage.

It is well documented in the prior art that a significant disadvantage inherent in PMMA IOLs resides in the fact that any brief, non-traumatic contact between corneal endothelium and PMMA surfaces results in extensive damage to the endothelium. See Bourne et al, Am. J. Ophthalmol., Vol. 81, pp. 482-485 (1976). Forstor et al, Trans. Am. Acad. Ophthalmol. Otolaryngol., Vol. 83, OP-195-OP-203 (1977); Katz et al, Trans. Am. Acad. Ophthalmol. Otolaryngol, Vol. 83, OP 204-OP-212 (1977); Kaufman et al, Science, Vol. 198, pp. 525-527 (1977) and Sugar et al, Arch. Ophthalmol. Vol. 96, pop. 449-450 (1978) for a discussion of the problem associated with implant surface/endothelium contact.

Since it is extremely difficult to avoid any contact between implant surfaces and endothelium during surgical procedures, efforts have been undertaken to modify the PMMA ocular implant surfaces to reduce the tendency thereof to adhere to and damage corneal endothelium.

Ocular implant surfaces have been coated with various hydrophilic polymer solutions or temporary soluble coatings such as methylcellulose, polyvinylpyrrolidone (Katz et al and Knight et al, supra), etc., to reduce the degree of adhesion between the implant surfaces and endothelial tissue cells. While offering some temporary protection, these methods have not proven entirely satisfactory since such coatings complicate surgery, do not adhere adequately to the implant surfaces, become dislodged or deteriorate after implantation, dissolve away rapidly during or soon after surgery or may produce adverse post-operative complications. Moreover, it is difficult to control the thickenesses and uniformity of such coatings.

Yalon et al [Acta: XXIV, International Congress of Ophthalmology, ed. Paul Henkind (1983)] attempted to produce protective coatings on PMMA implant surfaces by gamma-radiation induced polymerization of vinylpyrrolidone thereon [Se also Knight et al, Chem. Abs., Vol. 92: 203547f (1980]. Their efforts were not altogether successful, however, since their methods also presented problems in controlling the optical and tissue protective qualities of the coatings. Process conditions and parameters (i.e., monomer concentration solvent, dose and dose rate) were not specified. The resulting coating were of poor quality and non-uniform mechanical stability.

Gamma-PVP treatment of PTFE has been reported but under severe process conditions gamma doses above 1 Mrad are impractical in that both bulk and surface properties of the PTFE are changed [Boffa et al., J. Biomed. Mater. Res., 11, 317 (1977]. Non-aqueous solutions of high monomer concentrations (50% NVP in pyridine) are required at relatively high doses of gamma radiation (1-5 Mrad) resulting in a high degree of grafting with extensive changes in the bulk and surface properties of the PTFE since PTFE is readily degraded at gamma doses above 1 Mrad.

In application Ser. No. 037,153, filed Apr. 10, 1987, there are described improved methods for producing hydrophilic, gamma irradiation induced polymerized and chemically grafted coatings on ocular implants constructed of a variety of polymeric materials, which methods overcome the above-noted difficulties and disadvantages.

The invention described in that application is predicated on the discovery of certain process conditions and parameters that produce thin hydrophilic gamma irradiation induced polymerized and chemically grafted coatings of N-vinyl-pyrrolidone (NVP) [PVP], copolymerized NVP and 2-hydroxyethylmethacrylate (HEMA) [P(NVP-HEMA)], or HEMA [PHEMA] on the surfaces of ocular implants constructed of materials including polymethylmethacrylate (PMMA) and of other process conditions and parameters which produce thin gamma irradiation induced graft PVP, P(NVP-HEMA), or PHEMA coatings on the surfaces of ocular articles constructed of materials including polypropylene (PP), polyvinylidene fluoride (PVDF), polycarbonate (PC) and silicone (PSi). The coatings increase the hydrophilicity of the implant surface and minimize adhesion between the surface and sensitive ocular tissues such as corneal endothelium or iris thereby minimizing tissue damage and post-operative complications occasioned by contact between the implant surface and ocular tissue. The coatings produced by the improved method of the invention described in application Ser. No. 037,153 are thin and reproducibly uniform. Moreover, they are chemically bound to the surface of the ocular implant and, therefore, far more durable and less subject to removal, degradation or deterioration during or following surgery than the coatings produced by prior art methods.

The improved gamma-irradiation induced graft polymerization of NVP, HEMA or mixtures of NVP and HEMA on ocular implant surfaces comprising PMMA to form optimum PVP, P(NVP-HEMA) or PHEMA graft polymer surface modifications thereon comprises carrying out the graft polymerization in an aqueous solution under specific combinations of the following conditions:
  (a) monomer concentration in the range of from about 0.5 to about 50%, by weight;
  (b) total gamma dose in the range of from about 0.01 to about 0.50 Mrad;
  (c) gamma dose rate in the range of from about 10 to about 25000 rads/minute; and
  (d) maintaining the molecular weight of the polymer in solution in the range of from about 250,000 to about 5,000,000.

Optimally, the method may also be carried out under one or more of the following conditions:
  (e) substantially excluding free oxygen from the aqueous graft polymerization solution;
  (f) maintaining the thickness of the PVP or P(NVP-HEMA) surface graft in the range of from about 100A to about 100 microns;
  (g) including a free radical scavenger in the aqueous graft polymerization solution; and
  (h) including in the aqueous graft polymerization solution a swelling solvent for PMMA or other polymer substrate surface.

The improved gamma-irradiation induced graft polymerization of NVP, mixtures of NVP and HEMA or HEMA on ocular implant surfaces comprising PP, PVDF, PC or PSi to form optimum PVP or P(NVP-HEMA) surface grafts thereon may also be carried out under specific combinations of the process parameters as indicated above for PMMA but also under conditions which involve excluding free oxygen from the polymerization solution for preferred surface modification of these ocular implant polymer substrates.

At the present time, surgical instruments, medical devices, prosthetic implants, contact lenses and the like which are intended for contact with blood or with sensitive tissue surfaces are constructed of materials having the necessary physical properties to enable their use for the intended application; however, they suffer from the disadvantage that due to the generally hydrophobic nature of the blood or tissue contacting surfaces thereof, they exhibit undesired thrombogenic properties and significant damage is done to fragile or sensitive tissues by adhesion and manipulation or movement on contact with these instruments.

It is therefore an object of the present invention to provide an improved method for producing permanent, thin, uniform, tissue-protective hydrophilic surface modifications of plastic surgical instruments, medical devices, prosthetic implants, contact lenses and the like.

It is a further object of the invention to provide plastic surgical instruments, medical devices, prosthetic implants, contact lenses and the like having improved blood compatible and tissue-protective surface modifications thereon.

SUMMARY OF THE INVENTION

The present invention is predicated on the discovery of certain process conditions and parameters that produce thin, hydrophilic, gamma irradiation polymerized and chemically grafted coatings of N-vinylpyrrolidone(NVP [PVP]), copolymerized NVP and 2-hydroxyethylmethacrylate (HEMA) [P(NVP-HEMA)] or HEMA [PHEMA] on the surfaces of articles adapted for contact with living tissue of a human or non-human animal, e.g., surgical instruments, medical devices, prosthetic implants, contact lenses and the like constructed of a wide variety of plastic materials. For purposes of the following description of the invention, the term "tissue" is intended to include blood as well as solid tissue surfaces.

The surface modifications or chemically grafted coatings of this invention increase the hydrophilicity of the article surfaces and minimize adhesion between the surface and sensitive tissues such as blood cells, vascular endothelium, peritoneum, pericardium, etc., thereby minimizing tissue damage and complications occasioned by contact between the article and such tissues. The coatings produced are thin and reproducibly uniform. Moreover, they are chemically bound to the surface of the article and, therefore, are far more durable and less subject to removal, degradation or deterioration during or following utilization of the articles than the coatings produced by prior art methods.

The improved gamma-irradiation induced graft polymerization of NVP, HEMA or mixtures of NVP and HEMA on plastic article surfaces to form optimum PVP, P(NVP-HEMA) or PHEMA graft polymer surface modifications thereon comprises carrying out the graft polymerization in an aqueous solution under specific combinations of the following conditions:
  (a) monomer concentration in the range of from about 0.5 to about 50%, by weight;
  (b) total gamma dose in the range of from about 0.01 to about 0.50 Mrad;
  (c) gamma dose rate in the range of from about 10 to about 25000 rads/minute; and
  (d) maintaining the molecular weight of the polymer in solution in the range of from about 250,000 to about 5,000,000.

Optimally, the method may also be carried out under one or more of the following conditions:
  (e) substantially excluding free oxygen from the aqueous graft polymerization solution;
  (f) maintaining the thickness of the PVP or P(NVP-HEMA) surface graft in the range of from about 100A to about 100 microns;
  (g) including a free radical scavenger in the aqueous graft polymerization solution; and
  (h) including in the aqueous graft polymerization solution a swelling solvent for PMMA or other polymer substrate surface.

DETAILED DESCRIPTION OF THE INVENTION

Yalon et al (supra) and Knight et al (supra) disclose gamma-irradiation coatings on PMMA using N-vinylpyrrolidone (NVP) and 2-hydroxyethylmethacrylate (HEMA) and indicate poor dynamic (abrasive) protection of endothelium for these coatings. Dissolvable coatings of polyvinyl-alcohol (PVA) were regarded as optimal for intraocular lenses (IOLs) by Knight et al, supra, and commercial development of a PVA-coated IOL was attempted with unsatisfactory clinical results. The gamma polymerization surface modifications reported were carried out under process conditions of monomer concentration, solvent, dose and dose rate which were not specified and which apparently yielded poor quality, readily abraded coatings. Conditions for producing useful permanent PVP or PHEMA coatings on PMMA IOLs or any other plastic surface are not taught in the prior art. Neither Knight et al, Yalon et al or the literature on gamma-graft polymerization of the past 30 years suggest the process conditions required to achieve the complicated requirements for useful coatings on plastics. These requirements include:

(a) Thin, permanent, optically clear (in the case of contact lenses) and uniform graft coatings. The literature generally discloses conditions which produce distortion and degradation of the substrate due to the use of high gamma-radiation does (>1 Mrad) and non-aqueous solvent media, and yield thick, cloudy, non-uniform coatings (e.g., Chapiro, *Radiation Chemistry of Polymeric Systems*, John Wiley and Sons, Inc., New York, 1962; Henglein et al, Angew. Chem., 15, p. 461 (1958)).

(b) Long-term bioicompatibility in vivo.

(c) Low contact angle (high wettability) for water or underwater air bubble (less than about 30°).

(d) Non-adherent to tissue (adhesive force to endothelium less than about 150 mg/cm$^2$).

(e) Non-damaging to endothelium (less than ca. 20% damage for in vitro contact tests).

(f) Measurable graft coating by ESCA or FTIR analysis.

(g) Abrasion resistance by sliding (dynamic) friction testing showing no change in wetting (contact angle) and confirming before and after presence of graft coating.

(h) Rapid hydration—change from dry state to wetted lubricious state on immersion in water (within five minutes).

Yalon et al (supra) disclose an in vitro technique for measuring endothelium damage. Results for PMMA were used to illustrate the method. Although it was noted that PVP coatings reduced cell damage with less damage at higher monomer concentrations, the conditions for the experiment (i.e., irradiation dose, dose rate, etc.) were not disclosed nor were any of the critical process-product relationships indicated.

The improved process conditions and parameters of the present invention which are necessary to produce useful polymers having a surface modified by gamma-irradiation induced graft polymerization therein of PVP, P(NVP-HEMA) or PHEMA include: % monomer, gamma dose, dose rate, penetration time or swelling time of monomer into the substrate prior to polymerization, and oxygen (air) degassing. Other optimal process conditions include catalysts, free radical scavengers, polymer swelling solvents, and temperature. The solution polymer molecular weight and M.W. distribution, the % conversion and residual monomer, the graft polymer thickness and surface properties, etc., are process results which can change markedly as the process variables change. For example, the surface modification achieved for PVP on polymer surfaces will be different when using 10% monomer and 0.1 Mrad if prepared at low dose rate since low dose rates (slower polymerization) favor higher molecular weights. Similarly, degassed oxygen-free reaction media result in improved grafts at much lower doses. The presence of free radical scavengers such as copper or iron salts or organic reducing agents (i.e., ascorbic acid) also greatly influences other process parameters, generally reducing solution polymer molecular weight and preventing solution gelation at high monomer concentrations.

The method of the invention is applicable for the surface modification of medical instruments, devices, implants and contact lenses formed from a variety of plastic materials including, for example, poly-acrylates and -methacrylates (i.e., polymethylmethacrylate, polyethyl acrylate, polybutyl methacrylate, etc.); polyolefins (polyethylene, polypropylene, polybutadiene; SBS (styrene-butadiene), ethylene-propylene copolymers, (SE/BS) styreneethylene/butadiene), polycarbonates (PC) fluorocarbon polymers (i.e., polyvinylidene fluoride-PVDF, polytetrafluorethylene-PTFE, polyperfluoroethylenepropylene-FEP, polysiloxanes, various aliphatic and aromatic polyurethanes, including polyurethane polyester or polyether block copolymers, polyvinylchloride, and various polyesters including dacron PET.

Any instrument, device, implant, etc. constructed of one or more of the above materials may be surface modified according to the present invention to improve the tissue contacting characteristics of the surfaces thereof.

Plastic surgical instruments and implements such as probes, retractors, tissue and vessel separators, irrigation and aspiration tools, phacoemulsification tools, sponges, clamps, gloves, lens glides, positioning tools, forceps, insertion tools, staples, sutures, etc., may be treated in accordance with the present invention.

Medical devices such as hard and soft contact lenses, intravenous and central venous catheters, laser and balloon angioplasty devices, vascular and heart devices (tubes, catheters, balloons, ventricular assists, blood dialysis components, blood oxygenators, ureteral/urinary devices (Foley catheters, stents) (tubes and balloons), airway catheters (endotrachial and tracheostomy tubes and cuffs) enteral feeding tubes, wound drainage tubes, blood bags, and blood tubing may also be beneficially treated in accordance with the method of the present invention.

Implants which may be modified according to the present invention include, for example, vascular grafts, soft and hard tissue prostheses (mammary, cranio/facial, tendons, joints), heart valves and artificial hearts.

Modification of these instruments, devices, implants, etc. improve the surfaces thereof so as to improve blood compatibility and reduce tissue adhesion and tissue damage during surgical contact and manipulation. Moreover, the invention operates to reduce cell adhesion for reduced inflammation, reduce fibrous capsule formation for soft tissue implants, and reduce thrombogenicity for cardiovascular devices and prostheses. The invention also acts to reduce bacterial adhesion and thereby reduce the incidence of infection and further operates to reduce interfacial abrasion and friction which is of special value for joint and tendon prostheses.

Polyolefins and polyolefin/hydrocarbon block polymers are useful for constructing medical tubing, catheters, blood bags, sutures, etc. Copolymers of the SBS, EP, or SE/BS type may be thermoplastic elastomers which combine rubbery properties with extrudable or injection moldable processing properties. Surface modification of such materials according to the present invention is effective in changing the normal surface characteristics of these polymers from hydrophobic to hydrophilic.

The fluorocarbon polymers are widely used for catheters (i.e., intravenous catheters), for vascular prostheses (i.e., vascular grafts) and for coating medical devices, instruments and implants due to their biocompatability and inertness. However, the surface properties may be improved significantly according to the present invention to reduce cell and tissue adhesion, and improve blood compatability.

The silicone polymers are widely used for medical tubing and catheters, for mammary implants and other soft tissue prostheses. Hydrophilic surface modification, according to this invention, acts to reduce cell and tissue abrasion and adhesion and to thereby reduce fibrous capsule formation which is a major complication of soft tissue implants. Similarly, polyvinylchloride surface modification to produce more hydrophilic vinyl tubing and film surfaces can reduce thrombogenicity and improve biocompatibility of blood tubing, blood bags, cathethers, and other medical devices made of polyvinyl-chloride.

Polyurethanes which are used for such applications as pacer leads, intravenous catheters, enteral feeding tubes, vascular grafts, etc., are also beneficially modified by the process and materials of this invention to produce more hydrophilic surfaces and make such devices more biocompatible.

Each of the above-described process conditions and parameters of the method of the invention may be varied within the ranges discussed below to produce certain specific combinations which are particularly advantageous for the surface modification of a particulars polymeric surface. (a) Monomer concentration: Increasing monomer concentration increases polymer mol. wt. in the graft solution and reduces contact angle (C.A.), i.e., renders the surface more hydrophilic. For example, in the case of forming PVP coatings on PMMA, in the range of from about 3-15% NVP the PVP viscosity mol. wt (Mv) increases from 560,000 to 2,700,000 and the PMMA graft C.A. decreases from 29° to 21° at 0.1 Mrad and 309 rads/min. However, this effect is sensitive to dose rate and total dose. For example, at 1-10% NVP, but at a lower dose rate of 64 rads/min., the mol. wt. increases from 400,000 to 4,590,000 and the C.A. decreases from 49° to 18°.

In general, monomer concentrations in the range 0.5-50% are preferred depending on other parameters. For example, below 0.5%, even at low dose rate and high does, grafting is inefficient and C.A. below 30°-40° are not obtained. At monomer concentrations greater than 20-30%, effective grafting without solution polymer gelation requires low doses and use of free radical scavengers. Monomer concentrations greater than 50% are feasible but not preferred since high concentrations of radical scavengers must be used and polymer mol. wts. and monomer conversion are lowered significantly by their use. For producing PHEMA coatings, HEMA concentrations of between 0.5% and 10%, by weight, are sufficient.

(b) Dose: In general, increasing total gamma dose increases mol. wt. of the polymer and reduces C.A. However, an important practical limit exists in that at higher doses, lower dose rates, and higher monomer concentrations, reaction media becomes extremely viscous or form gels which are very difficult to wash and to remove (e.g., above 0.25 Mrad and 10% NVP at 309 rads/min).

(c) Dose rate: Decreasing dose rate increases solution PVP M.W., e.g., from 1,150,000 to 5,090,000 at 10% NVP and 0.1 Mrad as dose rate decreases from 1235 to 49 rads/min. The C.A. also goes down at lower dose rates, i.e., from 31° to 15°.

(d) Solution Polymer Mol. Wt.: Increasing $M_v$ generally produces lower C.A. grafts. However, $M_v$ greater than 5,000,000 or gels are generally impractical for grafting because of washing problems.

(e) Degassing: Removal of oxygen from the graft solutions by vacuum and/or inert gas (e.g., argon purging) has an important effect: lower total doses are required (practical grafting at less than 0.1 Mrad). Oxygen degassing also has a large effect on PVP $M_w$ and % conversion of monomer. For example, with degassing, good grafting of PVP on polypropylene (PP) is achieved at 0.05 Mrad and 10% NVP (C.A. 15°). Without degassing, little grafting occurs under these conditions. Oxygen degassing is critical to hydrophilic surface modification grafting where the substrate polymer is PP, PVDF, or PSi. It has been found that graft polymerization is inefficient when using these materials as substrates in the presence of oxygen. Oxygen degassing is also beneficial for PMMA and PC substrates in that much lower radiation doses (0.01-0.15 Mrad) become effective compared with grafting these polymers in the presence of oxygen.

(f) Graft thickness: Surface grafts less than 100-200 angstroms, although non-adhesive and hydrophilic, are useful but may exhibit somewhat less mechanical "softness" or compliant gel-like surfaces than thicker coatings for reduced tissue-contact trauma. Graft coatings greater than ca. 300-500 angstroms (or 0.03-0.05 microns) up to 50 microns or more are probably more desirable for many applications as long as they are smooth, uniform, optically clear for optic surfaces, and quickly hydrated.

Using no swelling solvents and no prolonged monomer contact with substrates prior to irradiation, surface grafts which exhibit desired implant properties under preferred process conditions have thicknesses of about 0.1 to 5 microns. However, using swelling solvents such as ethyl acetate, polymer grafts on PMMA of 100 microns or more can be prepared. For certain applications it may be preferred to have thicker "spongy" coatings of 20-100 microns.

(g) Free-Radical Scavengers: Free radical traps, usually reducing agents such as $Cu^+$, $Fe^{+2}$ ascorbic acid, etc., are known to inhibit radical polymerization in solution and thus be effective (especially at high gamma doses, high dose rates, and high monomer concentrations) in slowing the onset of solution gelation during grafting. However, under practical grafting conditions, this may result in lower mol. wts., high concentrations of unreacted monomer, and broad mol. wt. distributions. Use of metal salts may also be objectionable where maximum biocompatibility is critical.

Although most preferred graft conditions avoid the use of radical scavengers, useful conditions for graft coatings of PVP, P(NVP-HEMA) or PHEMA have also been defined using ascorbic acid to limit high viscosity and gelation of the graft polymer solution. These conditions use high monomer concentrations (up to 50%) and thicker grafts are obtained using ethyl acetate as a swelling solvent (0.5-5%).

(h) Swelling Solvents: The use of substrate polymer solvents in the aqueous monomer grafting solution facilitates swelling and monomer diffusion into the polymer before and during gamma polymerization. Penetration of monomers into the substrate increases graft coating thickness and enhances bonding to the surface. Solvents such as ethyl acetate have been shown to greatly facilitate this process with some substrates such as PMMA.

Although the above-described method represents a significant improvement over prior art methods, optimum results in each case depend upon the selection of a combination of numerous process parameters and conditions.

Where mixtures of NVP and HEMA are employed to form graft copolymerized coatings of P(NVP-HEMA), the mixtures may contain up to about 50% by weight of HEMA, based on the weight of the monomer mixture. However, above 20-30% HEMA, radical scavengers, and low monomer concentrations should be used to prevent gelation since HEMA enhances the onset of gelation.

It will be understood by those skilled in the art that the PVP, P(NVP-HEMA) or PHEMA graft coatings of this invention may be modified by copolymerization with various ionic monomers. Mixtures of hydrophilic and ionic monomers may also be copolymerized therewith. For example, graft copolymerization incorporating vinylsulfonic acids or vinylcarboxylic acids such as acrylic acid, crotonic acid or methacrylic acid can afford surface modifications which are anionic. Similarly, graft copolymerization incorporating aminofunctional monomers, e.g., vinylpyridines, aminostyrenes, or aminoacrylates, or aminomethacrylates such as dimethylaminoethylmethacrylate, or dimethylaminostyrenes afford surface modifications which are cationic.

Amounts of ionic monomers up to about 20% wt. % of the total monomer weight may be employed, it being understood that the critical process parameters listed above may be maintained.

Based on the foregoing considerations and the many process studies conducted, preferred conditions for various article substrate polymers by way of example are provided in the examples below. Some key points may be summarized as follows:

Several ranges of process conditions appear useful. Choice of the "best" process will depend on such factors as: molecular structure of substrate and coating thickness desired. In general, those conditions which produce extreme solution viscosities and gels or conditions which could produce solvent stress cracking or crazing of the IOL polymers (e.g., higher conc. than about 20% for a PMMA swelling solvent such as ethyl acetate) should be avoided. The following four sets of process conditions appear most practical for the preparation of improved surface modified ocular implants.

(1) Aqueous Monomer Concentration:
5-20% (preferred 10%)
Dose: 0.05-0.20 Mrad (preferred 0.10)
Dose Rate: 20-15,000 rads/min.
(preferred 50-2,000)
C.A. <30°
PVP M.W.: >250,000.

(2) Same as (1) except that system is oxygen degassed (vacuum or inert gas purge e.g. argon) with Dose: 0.01-0.15 Mrad (0.05 preferred) and % NVP: 1-15% (5-10% preferred). This system is generally preferred to (1).

(3) Same as (1) and (2) with swelling solvent (e.g. ethyl acetate for PMMA) gives greater monomer penetration of substrate and thicker grafts.

(4) High monomer concentrations (25-50%) using <5.0% ethyl acetate swelling agent and radical inhibitor such as ascorbic acid (0.1-1.0 mM) at 0.10-0.20 Mrad and 20-5000 rads/min.

All percentages expressed in the Examples are by weight unless otherwise stated.

All contact angles (C.A.) and other surface characterizations for gamma polymerization grafts, unless otherwise indicated, are for samples washed with water or water-alcohol at room temperature or elevated temperatures to remove soluble residual monomer and ungrafted polymer for the improved surface graft processes of this invention. The resulting graft polymers are stable and permanent for long-term use and are not dissolved by aqueous media.

EXAMPLE 1

This example illustrates the important effects which result from varying the above-discussed process conditions and polymerization parameters for gamma-irradiated polymer graft surface modification of PMMA with PVP.

PMMA slab samples were washed twice each by soap solution and distilled water using a sonicator. After complete drying the samples were put into NVP solutions in glass vials. The samples were then γ-irradiated at various conditions. After γ-irradiation, the surface modified PMMA samples were rinsed several times with $H_2O$ and evaluated.

The polymerized NVP grafting solutions or gels were freeze-dried under a vacuum. The solution PVP samples were evaluated for molecular weight by viscosity measurement ($M_v$) or gel permeation chromatography ($M_w$). For $M_v$, PVP was dissolved in distilled water and intrinsic viscosity, [η], was measured at 30° C. in a capillary viscometer.

PVP grafted PMMA samples were evaluated by water drop or underwater air bubble contact angle measurements. The bubble technique is regarded as more reliable for very hydrophilic surfaces. For air bubble C.A., the grafted PMMA was held horizontally in distilled water. An approximately 0.8 μl air bubble was formed and positioned underneath the test surface. Angles on opposite sides of the bubble were measured assuring symmetry. Five measurements were usually made for each sample. The results are set forth in the following tables:

TABLE 1

Dose Rate Effect on Solution Polymer Molecular Weight For γ-Polymerized NVP
Concentration: 10% NVP in $H_2O$
Total Dose: 0.1 Mrads

| Distance from $CO^{60}$ source | Dose Rate (rads/min) | Time (hrs. min) | [η] | Mol. Wt. ($M_v$) ($\times 10^6$) |
|---|---|---|---|---|
| 2" | 1235 | 1.21 | 1.48 | 1.15 |
| 4" | 309 | 5.24 | 2.21 | 2.27 |
| 6" | 137 | 12.09 | 2.61 | 3.04 |
| 8" | 77 | 21.36 | 2.85 | 3.49 |
| 10" | 49 | 33.45 | 3.56 | 5.09 |

The effect of dose rate was evaluated by PVP solution viscosity measurements. These results show that the molecular weight increased as dose rate decreased due to the slower and reduced initiation of radicals and the increased time of polymerization while maintaining the same total absorbed dose. At the lowest dose rate in this experiment, 49 rad/min (at 10" from the Cobalt-60 gamma source) the highest molecular weight PVP polymer, $M_v = 5.09 \times 10^6$, was obtained.

TABLE 2

Total Dose Effect on Molecular Weight of γ-Polymerized NVP
Concentration: 10% NVP in $H_2O$
Dose Rate: 309 rads/min (4" from γ-source)

| Total Dose (Mrads) | Time (hrs. min) | [η] | Mol. Wt. ($M_v$) ($\times 10^6$) |
|---|---|---|---|
| 0.05 | 2.42 | 1.86 | 1.69 |

TABLE 2-continued

Total Dose Effect on Molecular Weight of
γ-Polymerized NVP
Concentration: 10% NVP in $H_2O$
Dose Rate: 309 rads/min (4" from γ-source)

| Total Dose (Mrads) | Time (hrs. min) | [η] | Mol. Wt. ($M_v$) ($\times 10^6$) |
|---|---|---|---|
| 0.10 | 5.24 | 2.21 | 2.27 |
| 0.25 | 13.30 | * | — |
| 0.50 | 27.00 | * | — |

*Polymer solution gelled.

Table 2 shows the effect of total γ-irradiation dose on molecular weight at 309 rads/min. Increasing the total dose gives a higher molecular weight. A polymer gel was formed at a dose of 0.25 Mrad and higher. These results show that high irradiation dose can cause gelation or crosslinking of the PVP polymer.

TABLE 3

Molecular Weight of γ-Polymerized NVP at
Different Solution Concentrations
Total Dose: 0.1 Mrads
Dose Rate: 309 rads/min
γ-Irradiation time: 5 hrs. 24 mins.

| NVP Concentration (%) | [η] | Mol. Wt. (Mv) ($\times 10^6$) |
|---|---|---|
| 3 | 0.97 | 0.56 |
| 6 | 1.58 | 1.29 |
| 10 | 1.94 | 1.82 |
| 15 | 2.45 | 2.70 |

These results show the relation between the concentration of NVP monomer and the molecular weights of PVP at constant dose and dose rate. The results indicate that higher NVP concentrations give higher molecular weight polymers. The importance of dose rate is also indicated by the fact that even at 15% NVP, the PVP molecular weight ($M_v$) was only $2.7 \times 10^6$ at 309 rads/min. compared to $5.0 \times 10^6$ at a lower dose rate of 49 rads/min.

TABLE 4

Contact Angle of PVP γ-Grafted PMMA
at Different Dose Rates
Concentration: 10% NVP
Total dose: 0.1 Mrad

| Distance from γ-source | Dose Rate (rads/min) | Time (hrs. min) | Contact Angle |
|---|---|---|---|
| Ungrafted PMMA control | — | — | 65° |
| PVP Grafted PMMA | | | |
| 2" | 1235 | 1.21 | 31° |
| 4" | 309 | 5.24 | 24° |
| 6" | 137 | 12.09 | 21° |
| 8" | 77 | 21.36 | 19° |
| 10" | 49 | 33.45 | 15° |

The results in Table 4 show that the contact angles for PVP grafted PMMA decreased due to hydrophilic PVP grafting and that the lower dose rates give lower contact angles which is consistent with the increase in solution PVP molecular weight at lower dose rates.

TABLE 5

Contact Angles of PVP γ-Grafted PMMA
at Different Total Doses
Concentration: 10% NVP in $H_2O$
Dose Rate: 309 rads/min.

| Total Dose (Mrads) | Contact Angle |
|---|---|
| Ungrafted PMMA Control | 65° |
| Grafted PMMA | |
| 0.05 | 27° |
| 0.10 | 25° |
| 0.25* | 24° |
| 0.50* | 24° |

*Polymer solution gelled.

These results show the effect of total dose on the contact angles of PVP γ-grafted PMMA. The contact angle showed little change above 0.05 Mrad at constant dose rate of 309 rads/min.

TABLE 6

Contact Angles of PVP γ-Grafted PMMA
at Different Monomer Concentrations
Total Dose: 0.1 Mrad
Dose Rate: 309 rads/min

| NVP Concentration (%) | Contact Angle |
|---|---|
| Ungrafted PMMA Control | 65° |
| Grafted PMMA | |
| 3 | 29° |
| 6 | 27° |
| 10 | 25° |
| 15 | 21° |

The effect of different monomer concentrations was evaluated for PVP γ-grafts on PMMA by contact angle measurement. Even at 3% NVP and 0.1 Mrad a major increase in hydrophilicity was observed as compared with non-grafted PMMA. The contact angle decreased slightly at monomer concentrations above 3%.

TABLE 7

Molecular Weight of γ-Polymerized PVP
at Different Monomer Concentrations
Total Dose: 0.1 Mrad
Dose Rate: 64 rads/min.

| NVP Concentration (%) | [η] | Mol. Wt. ($M_v$) ($\times 10^6$) |
|---|---|---|
| 1 | 0.79 | 0.40 |
| 3 | 1.65 | 1.38 |
| 5 | 2.23 | 2.30 |
| 10 | 3.35 | 4.59 |

These results show the relationship between the concentration of NVP monomer and molecular weight of PVP at a dose rate of 64 rads/min.

The molecular weight of PVP increases significantly with increasing concentration of NVP monomer.

TABLE 8

Contact Angle of PVP γ-grafted PMMA
at Different Monomer Concentrations
Total Dose: 0.1 Mrad
Dose Rate: 64 rads/min.

| NVP Concentration (%) | Contact Angle |
|---|---|
| Ungrafted PMMA Control | 65° |
| Grafted PMMA | |
| 0 | 62° |
| 1 | 49° |
| 3 | 43° |
| 5 | 31° |

TABLE 8-continued

Contact Angle of PVP γ-grafted PMMA
at Different Monomer Concentrations
Total Dose: 0.1 Mrad
Dose Rate: 64 rads/min.

| NVP Concentration (%) | Contact Angle |
|---|---|
| 10 | 18° |

The contact angle of PMMA was evaluated after γ-grafting with NVP at different solution concentrations at a dose rate of 64 rads/min. These results show that the contact angles of PVP-grafted PMMA decreased with increasing concentration of NVP monomer. This result, at 64 rads/min dose rate is qualitatively similar to results at 309 rads/min (Table 6). Hydrophilicity at 10% monomer appears to be favored somewhat by the lower dose rate (C.A. 18° vs. 25°).

Polar organic solvents or aqueous-polar organic solvent mixtures may be useful for hydrophilic monomer graft polymerization. Typical of such organic solvents are alcohols or ethers such as methanol, ethylene glycol, polyethylene glycols, dioxane, etc. However, when such organic solvents act as radical traps or radical chain transfer agents, they must be used at concentrations lower than 50% or with high hydrophilic monomer concentrations (i.e., >25%). For example, methanol has some radical scavenger properties but may be used for PVP gamma grafts on PMMA in water-methanol mixtures up to 50-60% methanol for PVP grafts on PMMA using 0.1 Mrad and 10% monomer (Table 9). Hydrophilic grafts result although radical chain transfer by methanol appears to require low dose rates at 10% monomer.

TABLE 9

Contact Angle of PVP γ-grafted PMMA at
Different Dose Rates in 50% Methanol (MeOH) Solution
Concentration: 10% NVP in 50% MeOH
Total Dose: 0.1 Mrad

| Dose Rate (rads/min) | Contact Angle (degree) |
|---|---|
| No Graft | 65° |
| 1065 | 36° |
| 326 | 28° |
| 157 | 27° |
| 64 | 20° |

EXAMPLE 2

This example illustrates the effect of swelling solvents on the surface modification process.

For hydrophilic gamma grafts on PMMA as the substrate, for example, addition of the swelling solvent, ethyl acetate (EtOAc), to aqueous monomer solutions is advantageous to achieve more efficient diffusion of monomer into the PMMA surface. Although EtOAc is not very soluble in water, a homogeneous reaction medium can be achieved in the presence of a monomer such as NVP.

The thickness of the graft polymer surface modification can be increased by higher ethyl acetate concentrations and by longer diffusion times prior to irradiation; i.e., the time of preswelling. In general, without oxygen degassing, gamma radiation doses of 0.10-0.15 Mrad are suitable to achieve significant amounts of grafting.

The NVP-ethyl acetate-water solvent system is also a solvent for PVP and keeps the solution polymer phase homogenous.

"Embedded grafting" of PVP into the PMMA surface is made possible by irradiating the PMMA after exposure for various times to the monomer-swelling solvent-water mixture.

In experiments using this process technique, samples were cleaned by sonication in a 10% soap solution followed by washing with distilled water. Prior to surface modification, PMMA samples were dried for 18 hours in a vacuum desiccator and weighed. NVP monomer was purified by vacuum distillation and stored at 4° C.

For gamma radiation grafting, the PMMA substrate was immersed in aqueous monomer-solvent solutions and exposed to gamma radiation. Typically, cleaned substrates were immersed in NVP-ethyl acetate-$H_2O$ mixtures and irradiated in a 600 Curie Co-60 source. The samples were exposed to the monomer solution for various lengths of time. Gamma doses ranging from 0.01-0.15 Mrad as measured by Fricke dosimetry were used in this experiment. Dose rates were also varied. After irradiation, samples were removed from the gamma polymer solution and washed several times with distilled water and in deionized water with agitation. Some samples were weighed hydrated after blotting with filter paper to remove surface water and then dried for 24 hours in a vacuum desiccator. The polymerization solutions ranged from clear viscous solutions to gels. The following parameters were measured.

One measure of the degree of grafting was obtained from the weight increase of the substrate according to the following equation.

$$\text{percent grafting} = \frac{W_1 - W_o}{W_o} \times 100$$

where $W_o$ is the initial weight of PMMA and $W_1$ is the weight of grafted PMMA. Likewise, percent hydration was calculated according to the following equation.

$$\text{percent hydration} = \frac{W_w - W_d}{W_d} \times 100$$

where $W_w$ is the weight of PMMA after equilibration in water (after blotting it dry) and $W_d$ is the weight of dry sample (after desiccation). In most cases, the maximum water uptake was reached after 12 hours.

Captive air bubble and n-octane contact angles were measured for the radiation grafted PMMA surfaces to estimate the hydrophilicity of modified surfaces. Static contact angles were measured on a Rame-Hart contact angle gonimeter. At least five measurements on different surface regions of each sample were made.

IR/ATR surface analysis of the grafted and ungrafted surfaces was made by using a Perkin-Elmer Model 283B IR Spectrometer using attenuated total reflectance.

Samples of 1 $cm^2$ grafted and ungrafted PMMA were analyzed using a Kratos ES 300 ESCA spectrometer employing a magnesium Kα x-ray source. Graft analysis consisted of N/C ratio determination.

The molecular weights of PVP solution polymers were determined by solution intrinsic viscosity measurements at 30° C. in a Ubbelhode viscometer.

Radiation doses ranged from 0.01 to 0.15 Mrad and monomer concentrations ranged from 5 to 15%.

Data for PVP grafting onto PMMA using EtOAc as a swelling solvent are shown in Table 10. Since no pre-radiation swelling time is used here, diffusion penetration of the surface by EtOAc and monomer occurs during gamma radiation. Some pre-radiation swell-time is considered preferable. This system exhibits behavior typical of a reaction which involves monomer diffusion control. Partitioning of NVP monomer into the hydrophobic surface of PMMA is favored initially because of the presence of the ethyl acetate, which is a swelling solvent for PMMA.

By the use of a swelling solvent for the graft substrate (i.e., EtOAc), the NVP-EtOAc-H$_2$O system swells the surface layers of PMMA and polymerization grafting of monomer molecules in the vicinity of radiation induced radical species near the surface is immediate. Under such conditions, more efficient grafting is achieved at lower doses and with deeper penetration of the graft polymer into the solvent swollen surface.

Measurement of percent swelling of PMMA samples in NVP-ethyl acetate-H$_2$O (1:1:8) vs. time shows that swelling of about 6% is attained after 12 hours. In this system, the thickness of the grafted layer could be controlled by changing the time allowed for diffusion prior to irradiation, thus controlling the thickness of the grafted zone. Table 11 shows the graft behavior after 24 hours of pre-swelling of PMMA in 1:9 ethyl acetate: water containing 15% of NVP. Comparing this data with Table 10 (no swelling time), it is clear that the % graft is significantly higher for pre-swelling PMMA. At a given ethyl acetate concentration, this difference is generally more pronounced at lower monomer concentrations, e.g., 5% monomer compared to 15% monomer.

In this system, NVP is the monomer but also acts as a mutual solvent to maintain a homogenous phase of otherwise poorly miscible solvents, i.e., ethyl acetate and water. At a given monomer concentration (e.g., 10%), it is necessary to keep the concentration of ethyl acetate below 10% to avoid phase separation to a microemulsion. Variation of the ethyl acetate concentration, being a swelling agent, affects graft yield. Table 12 summarizes the observations made by varying the concentration of ethyl acetate while keeping other factors constant showing that the percent grafting does increase with higher ethyl acetate concentrations. Greater grafting efficiency is also indicated by the significant % grafting and reduction of C.A. in the solvent swelling monomer system at low doses. For example, up to 0.05 Mrad, little grafting occurs in a simple aqueous monomer system. In contrast, at only 0.01 Mrad C.A. is reduced to 35° (Table 11, 24 hr. preswell) and to 23° at 0.03 Mrad.

Techniques used for the chemical analysis of bulk polymers are usually not very satisfactory for analysis of the surfaces of polymers. The surface region, which is significantly different in structure and/or chemistry from the bulk, is present only as a fraction of the mass of the polymer. Thus, the traditional techniques of chemical analysis are inadequate. Special surface analysis techniques are required for graft copolymers since the surface region is a complex mixture of graft, substrate, crosslinking groups and chain transfer products. Two spectroscopic methods, ATR-IR and ESCA are the most useful methods now available for this purpose and were used to help characterize grafted surfaces.

The results for ATR-IR (attenuated total reflection infrared) shown in Table 13 indicate that the ratio of C=O (ester) and C=O (amide) groups in the surface changes from 7.67 to 1.68 as the gamma dose increases from 0.01 to 0.10 Mrad and then levels off which is consistent with PVP grafting on PMMA.

ESCA analyses are shown in Table 14 and indicate increasing nitrogen composition with increasing dose (and grafting) as expected for a PVP graft.

Scanning electron microscopic examinations of the grafted samples were performed in order to observe their surface morphologies. All of the coated surfaces appeared smooth even at 10,000X. The graft polymer surface modifications appear to provide uniform coverage across the surface of PMMA substrate. This is important to insure excellent retention of optical properties for an optical implant such an intraocular lens.

Major conclusions to be drawn from the results of this example are:

The NVP-ethyl acetate-water system produces uniform hydrophilic graft polymer surfaces with controllable graft penetration using PMMA as the substrate.

The monomer-ethyl acetate-water grafting front gradually penetrates into the substrate and may be controlled by varying the concentration of swelling agent and the time of pre-swelling.

The presence of the PVP surface graft was confirmed by gravimetric, contact angle, ATR-IR and ESCA measurements.

Unusually low radiation doses are required to achieve significant grafting. Hence, any possible radiation damage to the surface or substrate is minimized.

TABLE 10

Graft Polymerization of NVP on PMMA
Swelling time - 0 hours
Ethyl acetate : H$_2$O (1:9)

| Dose Rate (rads/min) | NVP Conc. | 0.01 Mrad | | 0.05 Mrad | | 0.10 Mrad | | 0.15 Mrad | |
|---|---|---|---|---|---|---|---|---|---|
| | | C.A. | % Graft | C.A. | % Graft | C.A. | % Graft | C.A. | % Graft |
| 309 | 5% | 48 | — | 47 | 0.5 | 42 | 0.7 | 36 | 0.7 |
| | 10% | 46 | 0.1 | 34 | 0.4 | 22 | — | 17 | 0.5 |
| | 15% | 40 | 0.2 | 32 | 0.5 | 16 | 0.9 | 18 | 0.5 |
| 77 | 5% | 40 | 0.2 | 38 | 0.2 | 41 | 0.6 | 38 | 0.3 |
| | 10% | 36 | 0.6 | 32 | 0.4 | 35 | 0.7 | 36 | 0.5 |
| | 15% | 38 | 1.1 | 25 | 0.5 | 28 | 0.8 | 26 | 0.6 |

TABLE 11

Grafting of NVP On PMMA: 24 Hours Swelling
Solvent - 9:1/H$_2$O-EtOAc/NVP - 15%

| | 309 rads/min | | 77 rads/min | |
|---|---|---|---|---|
| Total Dose (Mrads) | C.A. | % Graft | C.A. | % Graft |
| 0.01 | 38 | 1.0 | 35 | 1.3 |
| 0.03 | 27 | 2.3 | 23 | 2.8 |
| 0.05 | 17 | 2.5 | 17 | 2.4 |
| 0.10 | 16 | 3.0 | 16 | 3.2 |
| 0.15 | 10 | 3.2 | 16 | 3.4 |

TABLE 12

Graft Ploymerization of NVP on PMMA
Effect of Ethyl Acetate: 12 hours swelling
10% NVP, 309 rads/min

| Total dose | 3% EtOAc | | 6% EtOAc | | 10% EtOAc | |
|---|---|---|---|---|---|---|
| (Mrads) | C.A. | % Graft | C.A. | % Graft | C.A. | % Graft |
| 0.01 | 43 | 0.2 | 44 | 0.4 | 48 | 0.6 |
| 0.03 | 38 | 0.3 | 26 | 0.5 | 25 | 1.7 |
| 0.05 | 23 | 0.3 | 21 | 0.5 | 22 | 1.9 |
| 0.10 | 18 | 0.5 | 17 | 0.5 | 18 | 2.2 |
| 0.15 | 15 | 0.5 | 17 | 0.6 | 18 | 2.2 |

TABLE 13

ATR-IR Spectral Analysis of PVP Grafted PMMA Samples*

| Total Dose (Mrad) | $\nu_c = O$ (ester) / $\nu_c = O$ (amide) |
|---|---|
| 0.01 | 7.67 |
| 0.03 | 6.51 |
| 0.07 | 4.61 |
| 0.10 | 1.68 |
| 0.15 | 1.66 |

*Reaction mixture 5% NVP in 9:1 mixture of water-ethyl acetate, dose rate 1065 rads/min - Swelling time: 17 hours.

TABLE 14

ESCA Analysis of PVP Grafted PMMA Samples*

| Total Dose (Mrad) | N/C at 0° C. |
|---|---|
| 0.03 | $2.2 \times 10^{-2}$ |
| 0.05 | $3.1 \times 10^{-2}$ |
| 0.07 | $4.5 \times 10^{-2}$ |
| 0.10 | $4.7 \times 10^{-2}$ |

*Reaction mixture - 5% NVP in 9:1 mixture of water-ethyl acetate. Dose rate 1065 rads/min - Swelling time: 17 hours.

EXAMPLE 3

The following experiment demonstrates the very significant influence of oxygen on gamma polymerization and gamma grafting and the important beneficial effects of carrying out graft polymerizations in the substantial absence of oxygen.

Gamma radiation induced polymerization of NVP was carried out in 10% NVP aqueous solution as follows:

(a) polymerization in presence of oxygen (air);
(b) polymerization in absence of oxygen using argon degassing; and
(c) polymerization in absence of oxygen.

For Group (a), aqueous 10% NVP solutions were irradiated to total doses of 0.01, 0.05, 0.10, 0.20 and 0.25 Mrad in each case at 213 rads/min in the presence of air. An argon purge for 10 minutes was used in the case of (b). A vacuum freeze-thaw (FT) method was employed for degassing in the case of Group (c). In the freeze-thaw experiments, the monomer solution was frozen in liquid nitrogen and then vacuum (0.3 mm) was applied to eliminate oxygen. The frozen solution was thawed and brought to room temperature before irradiation. Some samples were subjected to three freeze-thaw cycles (3 FT). Experiments were run in duplicate to establish reproducibility.

To determine the oxygen degassing effects on gamma radiation grafting and polymerization, monomer conversions and molecular weights were determined for the different NVP solutions irradiated at 0.01 Mrad to 0.25 Mrad at 213 rads/min.

A method used for determining unreacted NVP after irradiation was as follows: 5 ml of the gamma irradiated NVP solution was extracted using 50 ml acetonitrile. NVP is soluble in acetonitrile but PVP is not. The PVP precipitate was centrifuged and the supernatant solution was analyzed for NVP. The NVP monomer solution (10% NVP/aqueous) was used as a control. NVP analysis was as follows: The 10% by weight aqueous solution was diluted with acetonitrile to appropriate concentrations (0.5 μg/ml to 5.0 μg/ml). The U.V. absorbance was measured for each solution at 323 nm to develop a standard curve of NVP concentration vs. U.V. absorbance. The regression coefficient was 0.99 for this curve. GPC was used for molecular weight measurements and gives $M_w$ as well as molecular weight distribution.

The % NVP conversion (amount of monomer reacted) is significantly affected by Ar purge deoxygenation and by FT oxygen degassing. At the very low dose of 0.01 Mrad virtually no polymerization occurs in the non-degassed oxygen (air) containing solutions. However, 46%, 61% and 63% conversion to PVP occurred for the Ar-purged, 1FT and 3FT samples, respectively. Even at 0.10 Mrad, samples irradiated in air showed only 90% conversion (10% unreacted NVP monomer) compared to virtually complete conversion (99%) for oxygen degassed systems. This is important for biological implants where unreacted monomers can cause serious adverse toxicological behavior.

To demonstrate more efficient grafting of PVP on PMMA at low gamma doses in the oxygen degassed system, 10% aqueous NVP was argon purged to remove oxygen and irradiated with PMMA samples at 157 rads/min to 0.05 Mrad. The resulting hydrophilic surface modification had C.A. 20° and was stable (no change in C.A.) to mechanical abrasion. As indicated above, this mechanically stable and very hydrophilic graft of PVP on PMMA graft is achieved with high monomer conversion (98%) and a high degree of polymerization for the solution polymer ($1.65 \times 10^6$ mol. wt.). In the presence of air (oxygen) higher radiation doses (>0.1 Mrad) and/or higher monomer concentration (15% or more) are required to achieve low C.A. with high conversion and high molecular weight. For hydrophilic monomer gamma polymerization grafts on other substrate polymers, i.e., polypropylene, fluorocarbons (e.g., PTFE or PVDF), or silicones, the beneficial effect of oxygen degassing can be even greater. Oxygen removal may also be used for improved gamma grafting in combination with the use of substrate swelling solvents and free radical inhibiting agents such as oxidizable metal salts or organic compounds (e.g., ascorbic acid).

PVP molecular weight is also greatly affected by oxygen degassing. The Ar-purged and FT samples yield PVP polymers with molecular weights of about $1.6 \times 10^6$ at only 0.01 Mrad. In sharp contrast, the non-degassed samples do not form any measurable polymer. At 0.05 Mrad, oxygen degassed samples yield PVP with molecular weights of $1.65-1.8 \times 10^6$ compared with only about $0.35 \times 10^6$ in air. At 0.10 Mrad, all samples have molecular weights of about 1.8 to $2.0 \times 10^6$.

EXAMPLE 4

The following experiments were carried out to demonstrate the advantageous effects of free radical scavengers in inhibiting gelation during the graft polymerization process, especially at high monomer concentrations.

PMMA samples were surface grafted with PVP using gamma irradiation as in Example 1. Ascorbic acid (AscA) was used as a radical inhibitor in these experiments. The irradiation conditions are set forth in Table 15.

TABLE 15

| | |
|---|---|
| (a) | 30% NVP/0.5mM AscA/2.5% EtoAc/0.2 Mrad* |
| (b) | 30% NVP/0.5mM AscA/2.5% EtoAc/0.15 Mrad |
| (c) | 40% NVP/1.0mM AscA/0.1 Mrad |
| (d) | 50% NVP/1.0mM AscA/0.1 Mrad |
| (e) | 50% NVP/1.0mM AscA/0.2 Mrad* |

*0.1 Mrad initial dose; additional 0.1 Mrad after washing sample free of monomer and soluble polymer.

C.A. for all PMMA samples in Table 15 were 18°–24° indicating very hydrophilic grafts. Dose rates used were 33 rads/min. A dose rate of 667 rads/min for (b) was also used. Solution polymer gelation occurs at these monomer concentrations (30–50%) if a radical inhibitor such as AscA is not used. In addition to C.A., PVP grafting was verified by ESCA and FTIR-ATR analysis showing the presence of surface nitrogen and the PVP imide carbonyl group. Good mechanical properties were demonstrated by an abrasion test showing little change in C.A. or surface nitrogen after abrasion.

EXAMPLE 5

This example demonstrates the large favorable effect of hydrophilic gamma graft surface modification on reducing tissue adhesion by measuring corneal endothelium adhesion, and cell adhesion using fibroblast cells. These are important factors in demonstrating the improved biocompatibility and minimal tissue irritation or damage afforded by the hydrophilic graft surface modifications of this invention.

An apparatus which measures the force of adhesion (mg/cm$^2$) between contacting polymer and tissue surfaces was used to determine adhesion between rabbit corneal endothelium and polymer surfaces. Adhesion force values of about 250–400 mg/cm$^2$ were measured for PMMA and other hydrophobic polymers evaluated for implants, i.e., silicone, polypropylene, etc. The improved hydrophilic gamma graft surfaces, prepared under preferred process conditions, exhibit much lower adhesion; below 150 mg/cm$^2$ and often less than 100 mg/cm$^2$. This is accompanied by a major reduction in endothelium cell damage as measured by SEM; from about 50–80% damage for PMMA or silicone to 20% or less for surfaces gamma grafted under preferred process conditions of this invention.

The gamma graft surface modifications of this invention also show a major reduction in cell adhesion as demonstrated by exposure to live cell cultures of chick embryo fibroblasts (CEF). Experiments indicate that 3–4 times more CEF cells adhere to PMMA as compared to PVP graft modified PMMA. Grafts prepared at 0.1 Mrad and using 15% NVP, for example, showed adherence of only 35% of the number of CEF cells which adhere to PMMA. Similarly, PHEMA grafts on PMMA exhibited only 38% cell adhesion and 15:1 NVP: HEMA (at 16% total monomer) exhibited only 20% CEF cell adhesion compared to PMMA. Using rabbit lens epithelial cell cultures, it was also shown that the hydrophilic polymer graft surfaces exhibited virtually no cell adhesion compared to 10–25 cells per mm$^2$ adherent to hydrophobic polymer substrates such as polycarbonate, PMMA and polysiloxanes.

EXAMPLE 6

This example demonstrates the graft polymerization of HEMA and mixtures of NVP and HEMA on PMMA.

The method of Example 1 was repeated utilizing a 16% NVP/HEMA (15:1) aqueous solution at about 1300 rads/min and 0.10 Mrad dose. The PVP-PHEMA surface modified PMMA had a C.A. of 17°. Under similar conditions, a 7% NVP/HEMA solution (5:2) gave a surface with C.A. 23°, and a 2.5% HEMA solution gave a surface with C.A. 18°.

EXAMPLE 7

This example demonstrates the graft copolymerization of anionic or cationic monomers with the hydrophilic monomers of this invention using ionic monomers with NVP.

The method of Example 1 was used with PMMA substrate and 15% NVP plus 1–5 wt% of acrylic acid (AA) or crotonic acid (CA) as comonomers at 0.1 Mrad and 1235 rads/min. Contact angles were 18–22° and endothelium adhesion was about one half or less that of unmodified PMMA indicating formation of a good hydrophilic graft coating. Similar results can be obtained using dimethylaminoethylacrylate to produce cationic graft coatings.

EXAMPLE 8

This example demonstrates the hydrophilic monomer surface grafting of polypropylene (PP) and the importance of oxygen degassing for effective surface modification.

Hydrophilic surface grafts on polypropylene are not readily prepared by gamma irradiation of aqueous NVP in the presence of oxygen. Under conditions of Example 1, even at gamma doses >0.1 Mrad and monomer concentrations >10%, little surface hydrophilicity and little reduction in C.A. occurs. However, in oxygen degassed media, at 157 rad/min, and doses as low as 0.01–0.05 Mrad with 10% NVP, contact angles were about 15°. Very hydrophilic PP grafts which are also mechanically stable by a mechanical abrasion test are thereby readily prepared using oxygen degassed process conditions. This is especially important for gamma graft surface modification of IOLs with PMMA optics and PP haptics.

EXAMPLE 9

Surface modification of polycarbonate is most readily accomplished using gamma radiation of oxygen degassed aqueous monomer NVP solutions, e.g., grafting conditions of oxygen degassed 10% NVP at 93 rad/min and 0.05 Mrad dose yield C.A. 19°.

EXAMPLE 10

Although silicone (PSi) does not gamma graft with NVP as readily as PMMA, PSi surfaces were modified using oxygen degassed 10% NVP solutions. Irradiation to 0.05 Mrad at 93 rad/min yields C.A. of about 45° indicating significant surface hydrophilicity. Higher doses, swelling solvents, higher monomer concentrations, and different hydrophilic monomers can produce improved hydrophilicity. For example, gamma grafting of NVP/HEMA (10:1) at 0.10 Mrad and 157 rad./min even without oxygen degassing yields grafts with 30° C.A.

EXAMPLE 11

Polyvinylidene fluoride (PVDF) is an example of a fluorocarbon polymer which can be surface modified by gamma irradiation of aqueous NVP, NVP/water-methanol solutions or EtOAc-water systems. Hydrophilic grafts, with C.A. about 30°, are prepared at 326 rad/min and 0.20 Mrad. However, PVDF is preferably grafted using oxygen degassed process conditions. Conditions of 157 rad/min, 0.05 Mrad, and 10% aqueous NV produce PVP grafts with C.A. 17°. Since NVP monomer is also an effective swelling solvent for PVDF, allowing pre-radiation swelling time is favorable for producing improved grafts. For example, C.A. as low as 14° is obtained using 5 hrs. swelling time with 7% NVP, 0.10 Mrad and 94 rads/min.

EXAMPLE 12

Hydrophilic Surface Modification of FEP Teflon Intravenous Catheter Polymers by γ-PVP and γ-PVP/HEMA FEP teflon is a fluorocarbon polymer which is used for a number of medical devices such as intravenous catheters. It is very hydrophobic with a contact angle greater than 95° and shows significant tissue adhesion and damage on contact as indicated by in vitro rabbit corneal endothelium tests: about 250 mg/cm$^2$ adhesion force and 30-50% cells destroyed. FEP teflon film was surface modified by the following procedure to produce hydrophilic surfaces with contact angles less than 30-40°, with tissue adhesion reduced to less than about 120 mg/cm$^2$, and tissue damage reduced to less than 20%. For example, FEP films immersed in 25% aqueous NVP monomer and irradiated to gamma doses 0.10 and 0.25 Mrad (without oxygen degassing) yield hydrophilic PVP graft surfaces with contact angles of 33° and 26° respectively. The endothelium adhesion force was 45 mg/cm$^2$ for the latter sample and FTIR-ATR spectroscopy verified the presense of the PVP surface graft. FEP intravenous catheters exhibit improved surface properties when hydrophilic surface modified by the materials and processes of this invention; i.e., reduced pain and insertion force, reduced vascular endothelium damage, improved blood compatibility, and reduced susceptibility to adherence of pathogens and associated infections. Central venous cathethers and heart catheters are also beneficially surface modified in this manner. Other fluorocarbon polymer catheters (e.g., PTFE) are similarly improved by this hydrophilic surface modification.

A further improvement in the γ-graft process for hydrophilic surface modification of fluorocarbon polymers is achieved through a surface pre-treatment with a defluorinating agent such as sodium naphthalene. For example, exposure of PTFE to a sodium naphthalene solution for only 30-60 seconds followed by γ-grafting of PVP or HEMA resulted in grafts with improved wettability as compared with no pre-treatment and contact angles of 18° for 10% aqueous NVP and 0.1 Mrad, 22° for 1% HEMA and 0.005 Mrad, and 19° for 10% NVP/HEMA and 0.01 Mrad.

EXAMPLE 13

Hydrophilic Surface Modification of Porous PTFE Vascular Graft (Goretex ™) by γ-PVP Process Porous PTFE vascular grafts are presoaked in acetone, acetone-water-monomer solutions and then irradiated immersed in an aqueous monomer solution; typically 10% NVP, 5% acetone, 85% water in a gamma source to 0.02-0.15 Mrad total dose. After thorough washing with water, the PTFE was characterized and shown to have a hydrophilic surface modification by a major reduction in contact angle (from 98° unmodified to about 20° for the PVP surface graft). The PVP surface modification is also shown by FTIR-ATR surface spectroscopy. The mechanical properties of the fluorocarbon polymer substrate are virtually unchanged by the very low gamma radiation doses required for hydrophilic polymer grafting. The surface modification is shown to have little effect upon the porous structure of the PTFE vascular graft by scanning electron microscopy.

The resulting hydrophilic surface modified PTFE and porous vascular graft materials exhibit improved blood compatibility properties of special value for small diameter vascular grafts and for other blood contacting implants and devices, i.e., heart valves, ventricular assists, artificial hearts, vascular catheters, and pacer leads.

The very low doses of this invention do not damage or change the bulk properties of PTFE substrates and the use of low gamma doses with aqueous polymerization media results in very thin uniform hydrophilic surface modifications with retention of the substrate structure and physical properties, i.e. the pore structure of porous vascular graft PTFE materials.

EXAMPLE 14

NVP-HEMA Copolymer Gamma Grafting on FEP Teflon

NVP-HEMA copolymer gamma-grafting of FEP teflon was found to be very efficient at NVP:HEMA ratios of 9:1 and 8:2 yielding very hydrophilic surface modification with 10% aqueous monomer solutions and 0.1 Mrad (contact angles of 30° or less). At 8:2 NVP:HEMA and 10% monomer, contact angles less than 30° can be achieved at less than 0.05 Mrad. Hydrophilic surface modified FEP teflon intravenous catheters are readily prepared by this method to yield catheters with reduced insertion force and pain, and which are less likely to exhibit i.v. catheter complications such as infection, phlebitis, clotting, etc.

EXAMPLE 15

Surface Modification of Polyurethanes

Polyurethanes (PUR) have become increasingly important polymers for medical devices and implants, especially for i.v. catheters, pacer leads, vascular grafts, and artificial heart applications. Although PURs are generally more hydrophilic than silicones or fluorocarbons, they do not generally exhibit the significant reduction in tissue adhesion and low tissue damage properties of more hydrophilic graft polymer surface modifications, i.e. PVP gamma grafts. Improved surface properties for medical devices and implants is achieved by the gamma-irradiation surface modification process of this invention.

For example, films of a 55 durometer polyurethane polyether block copolymer (Pellthane 5363) were gamma irradiated to 0.1 Mrad in oxygen degassed 10% aqueous NVP to yield significantly more hydrophilic surfaces. The unmodified contact angle of 54 was reduced to 28° for the PVP surface modified PUR. In vitro endothelium contact damage tests for PURs yield cell damage results averaging 60% or more compared to cell damage of less than 20% which is found for the hydrophilic PVP surface modifications. This improvement in PUR surface properties is especially important for commonly used radio-opaque PUR formulations containing such additives as barium sulfate because such formulations tend to have poorer biocompatibility. A typical PUR (Pellthane) formulation containing about 12% BaSO$_4$, for example, exhibits very high endothelium contact damage (80%) which is greatly reduced (<30%) by hydrophilic polymer surface modification.

TABLE 16

Some Tissue Damage Data Using In Vitro Rabbit Endothelium Contact Testing For Different Polymers Compared to Hydrophilic PVP Gamma-Grafts

| | Contact Angle | % Endothelial Cell Damage |
|---|---|---|
| PMMA | 65–72° | 60–80% |
| FEP Fluorocarbon | 95–105° | 30–50% |
| Silicone | 90–100° | 60–80% |
| Gamma-PVP on PMMA | | <20% |
| Gamma-PVP on Silicone | | <20% |
| Gamma-PVP on FEP fluorocarbon | | <20% |

It is conventional for many medical device polymers to be filled with barium or bismuth radio-opaque compounds (i.e. BaSO$_4$) to enable X-ray examination. This can make surfaces even more damaging to tissues. Surface modification according to the method of the present invention is especially beneficial for such radio-opaque polymer compositions to provide smoother, tissue-protective, more biocompatible surfaces.

EXAMPLE 16

Hydrophilic Surface Modified PMMA Contact Lenses

This example illustrates the beneficial tissue-protective properties obtained by hydrophilic polymer surface modification of conventional hard (PMMA) contact lenses. Such contact lenses are normally irritating and abrasive to the external corneal epithelium. PMMA contact lenses are surface modified by gamma-graft polymerization immersed in aqueous NVP monomer (typically 10% NVP) using 0.1 Mrad dose. The resulting transparent hydrophilic graft make the contact lens surface water wettable (<30° C.A.) and non-adherent to the epithelial surface thereby reducing epithelial abrasion and irritation. The various process improvements of this invention may be readily adapted to produce contact lenses with controlled surface modification thickness suited to specific patient needs.

EXAMPLE 17

Hydrophilic Surface Modified Silicone Soft Contact Lens

Silicone soft contact lenses are widely used due to their mechanical flexibility and good oxygen permeability. However, silicone is normally hydrophobic. It is, therefore, not water wettable and may adhere to or abrade sensitive corneal epithelial tissue. Many types of silicone contact lenses are surface-treated with an oxidizing plasma to increase water wettability and minimize this problem. However, this type of surface oxidation has only a slight tissue-protective value and is usually transient in aqueous media. The silicone surface loses its hydrophilicity and becomes less wettable, often within a few weeks. In contrast, the hydrophilic polymer surface grafts of this invention are permanently bound chemically and persist indefinitely to maintain excellent water wettability. Furthermore, they exhibit non-adherent, lubricious, tissue-protective qualities in contact with the corneal epithelium thereby minimizing abrasion and irritation while retaining the favorable optical, mechanical and oxygen permeability properties of the polysiloxane.

Commercially available silicone contact lenses are readily surface modified under conditions noted in Example 10. Typically silicone contact lenses are gamma-irradiated in 10% aqueous NVP-HEMA (10:1) to 0.1 Mrad to yield a hydrophilic surface modification with a C.A. less than 35° which is stable in aqueous media and which is significantly less irritating to the corneal epithelium.

EXAMPLE 18

Hydrophilic Surface Modified Endotracheal Tubes and Cuffs

Endotracheal and tracheostomy tubes are conventionally made of silicones, polyurethanes, fluorocarbon polymers and polyvinyl chlorides. Balloons or cuffs on these airway devices are inflated during intubation and are usually made of latex rubber, vinyl, or silicone polymers. Significant clinical problems associated with the use of these devices are desquamation of the ciliated cells of the trachea and even more severe damage to the trachea due to the pressure, irritation and adhesion of the cuffs. Post-operative infections are associated with adherence of pathogens to the damaged and denuded areas of the trachea caused by the airway tube cuffs. Hydrophilic polymer surface modification of the tube and cuff surfaces according to this invention affords a significant improvement in these devices by minimizing abrasive contacts and adhesion to the sensitive tracheal tissues.

A silicone cuff is modified with PVP-PHEM (10:1) by the methods of Example 10. The resulting hydrophilic cuff has markedly reduced adhesion to tissue and causes less tracheal irritation and damage than hydrophobic polysiloxane cuffs. Similarly, a latex rubber cuff is modified with gamma-grafted PVP according to the method of Example 8. The resulting hydrophilic cuff is less adherent to sensitive tracheal tissue than normal hydrophobic latex rubber cuffs causing less tracheal irritation and damage during intubation.

EXAMPLE 19

Hydrophilic Surface Modification of Foley Catheter Tubes and Balloons

Foley catheter tubes and balloons are used for catheterization of the urinary tract and conventionally made of the same hydrophobic polymers used for endotracheal tubes and cuffs as noted in Example 18. Clinical complications associated with such devices are tissue irritation, infection, and encrustation due to the tissue adherent and damaging surface properties of the hydrophobic catheters and the adherence of pathogens, proteins, and minerals to the surfaces. Although silicone and fluorocarbon polymers tend to exhibit reduced mineral deposits and encrustation, hydrophilic polymer surface modification affords improved resistance to the problems of tissue irritation, infection and encrustation.

A silicone Foley catheter is modified with PVP-PHEMA (10:1) according to the methods of Example 10. The resulting hydrophilic surface modified catheter has reduced tissue adhesion and exhibits less encrustation than unmodified silicone. In another example of the advantages of this invention, a Foley catheter with a latex balloon is surface modified according to the method of Example 8 yielding a hydrophilic surface which is less likely to promote infection and is less susceptible to encrustation.

EXAMPLE 20

Hydrophilic Surface Modification of Surgical Gloves and Sponges

Latex rubber surgical gloves exhibit hydrophobic surface properties and tend to adhere to sensitive tissue surfaces thereby enhancing manipulative damage to tissues in all types of surgery. Manipulative damage can result in increased post-operative complications such as infection and surgical adhesions. Hydrophilic surface modification of surgical gloves results in reduced tissue adhesion of the rubber latex and less chance of severe manipulative tissue trauma due to contact with gloves. Latex rubber gloves are surface modified with a hydrophilic PVP surface according to the method of Example 8. The very low gamma-dose required by the process of this invention makes it feasible to accomplish this hydrophilic polymer grafting without altering the mechanical properties of the radiation-sensitive rubber latex. The resulting hydrophilic latex surgical gloves are less adherent and less damaging to sensitive tissue normally contacted during surgery; i.e., peritoneum, pericardium, etc.

Surgical sponges and gauzes used in surgical procedures are also damaging to tissue due to tissue adhesion and abrasion. Sponges and gauzes are normally made of cotton, polyesters, cellulosic material and polyurethanes. These natural and synthetic polymers are all amenable to hydrophilic surface modification by the materials and processes of this invention. In a typical example, a cotton gauze sponge is surface modified by gamma-grafting with PVP using 10% aqueous NPV and 0.1 Mrad dose. The sponge surface is thereby rendered more hydrophilic and less abrasive to tissue during surgical manipulation without altering the structure and function of the sponge.

EXAMPLE 21

Hydrophilic Surface Modification of Silicone Mammary Prosthesis

Mammary prostheses are most commonly constructed of a hydrophobic polysiloxane skin or membrane containing air, water or silicone gels or fluids. A major complication of such soft tissue prostheses is the irritation and inflammatory process which occurs at the tissue-implant interface which leads to formation of a hard fibrous capsule surrounding the implant. This fibrous capsule can severely compromise the bioacceptance of the prosthesis and, if severe, can lead to tissue necrosis, extrusion and loss of the implant. The hydrophilic surface modification of the silicone which is accomplished by this invention leads to reduced tissue irritation and abrasion by the implant and reduced adhesion of infiltrating cells during the postoperative period which normally can lead to extensive fibrous capsule formation. A silicone bag/silicone gel mammary prosthesis is surface modified with a hydrophilic PVP-PHEMA graft according to the method of Example 10. This hydrophilic prosthesis surface is less adherent to tissue or cells as compared to normal silicone and thereby has improved biocompatibility with less tendency to form a surrounding hard fibrous capsule.

EXAMPLE 22

Hydrophilic Surface Modification of Carbon Fiber Composite Reinforced Polycarbonate Surgical Instrument Plastic surgical instruments made of various hydrophobic structural polymers are used to an increasing extent because plastics lend themselves to high quality—low cost manufacture of special value for disposable instruments. Such instruments may exhibit significant tissue adhesion with accompanying manipulative trauma. Improved tissue-protective properties are achieved by the hydrophilic polymer surface modification of this invention. Fiber reinforced composites are among the most important examples of plastic materials used for instruments (containing glass, carbon or boron fibers to provide rigidity and high mechanical strength). A carbon fiber reinforced bisphenol-A polycarbonate microsurgical forcep for surgical insertion of an ocular implant is an example of a surgical instrument which is significantly improved by this invention. Using the process of Example 9 for the polycarbonate polymer, the carbon fiber reinforced polycarbonate instrument is readily surface modified with PVP. The resulting instrument surface is much less adherent to tissue and less damaging in contacts with fragile ocular tissues. Additionally, the surface modified plastic instrument is less likely to scratch or damage the surface of plastic ocular implants.

EXAMPLE 23

Hydrophilic Surface Modification of Silicone Irrigation/Aspiration (I/A) Tools Used in Ophthalmic Surgery In ophthalmic surgery, I/A tools are used to irrigate the eye with irrigating solutions and to aspirate fluids and tissue debris out of the eye. Silicone tips are commonly used on such I/A instruments. They are maneuvered around the anterior and posterior chambers of the eye with resulting frequent contacts with fragile tissues. For hydrophobic silicone devices, these tissue contacts may cause significant tissue damage which can compromise the success of the ocular surgery.

Silicone I/A tips are surface modified with PVP and PVP-PHEMA by the process of Example 10. The resulting hydrophilic polymer surface is less adherent to tissue and less damaging on contact with sensitive tissues during surgery.

EXAMPLE 24

Hydrophilic Surface Modification of Polyurethane Artificial Heart

Implants or ex-vivo heart assist and artificial heart devices are most often constructed of woven fiber reinforced segmented polyether polyurethanes because of their superior mechanical strength properties. However, these materials are still thrombogenic to a significant degree and clotting complications severely limit the use of such devices. Modification of the surfaces of such devices with hydrophilic polymer grafts which are less thrombogenic by virtue of low blood cell and platelet adhesion and activation, low fibrinogen adsorption, etc., is efficacious in prolonging the useful life of such devices and implants. A polyurethane Jarvic-7-type artificial heart is readily surface modified with a PVP graft by the process of Example 15. This process is uniquely suitable for the uniform hydrophilic surface modification of highly irregular complex structures such as the artificial heart since the entire device is immersed in the monomer solution and radiation permeates the entire structure to uniformly activate the substrate and initiate surface graft polymerization in a controlled manner.

EXAMPLE 25

Hydrophilic Surface Modification of Polyvinylchloride (PVC) Catheters

PVC is widely used for catheters, blood tubing, blood bags, and many other medical devices. Formulations are hydrophobic and exhibit some adverse tissue adhesion and cell adhesion behavior. Hydrophilic surface modification is useful in improving blood and tissue compatibility. Since formulation often contain significant concentrations of plasticizers (i.e., dioctyl phthalate), leaching of surface plasticizer by washing with appropriate solvents such as aqueous acetone prior to gamma graft surface modification is preferred. After aqueous acetone washing, a PVC vascular catheter is exposed to 0.1 Mrad immersed in degassed 10% aqueous NVP to yield a hydrophilic PVP graft which exhibits less vascular endothelium damage on contact and which is less thrombogenic than unmodified PVC.

EXAMPLE 26

Hydrophilic Grafting of Medical Devices Having Combinations of Materials

One of the important aspects of this invention is the discovery that certain grafting process conditions make it feasible to surface modify combinations of materials to be used in medical devices. Surface grafting of an assembled device can then take place in a one-step simultaneous grafting procedure yielding improved, more biocompatible surfaces. Material combinations of PMMA, PC, PUR, fluorocarbons, PP, PSi and other polymers can thereby be grafted under conditions of this invention. Table 17 summarizes some device combinations with preferred mutual grafting conditions for obtaining improved PVP grafts.

PMMA/PP and PMMA/PVDF

It has been demonstrated that PMMA and PP gamma graft under degassed conditions at 157 rad/min, 0.05 Mrad, 10% NVP. These conditions yield contact angles of 20° and 15° for PMMA and PP, respectively, and are mechanically stable. Non-degassed PP does not graft efficiently under conditions similar to PMMA because of the adverse effect oxygen has on PP surface grafting.

PVDF surface graft studies also indicate the importance of oxygen degassing. A 10% degassed aqueous NVP solution, irradiated at 157 rad/min to 0.05 Mrad, gives good hydrophilic grafts on both PMMA and PVDF. See Table 17.

PC/PP and PC/PVDF

PC and PP graft under similar gamma irradiation conditions when NVP solutions are degassed. Using 157 rad/min, 0.05 Mrad, and 10% aqueous NVP solutions, efficient hydrophilic grafting occurs on both polymers yielding contact angles of 19° and 15°, respectively.

PVDF and PC are both grafted under the same conditions which graft PC/PP and PMMA/PP combinations; e.g., 157 rad/min, 0.05 Mrad, 10% degassed NVP. Since PVDF swells in NVP, gamma grafting with prior swelling time can result in improved binding of PV to the PVDF. Conditions are thereby afforded for simultaneous hydrophilic polymer grafting to devices which are made of two or more polymers as indicated above. See Table 17.

TABLE 17

Surface Modification of Medical Device Combinations with PVP

| Polymer Combination | Typical Preferred Gamma Polymerization Grafting Conditions* |
|---|---|
| PMMA/PP | a. 10% degassed NVP, low dose rate (LDR)**, 0.05 Mrad. |
| | b. 2.5% EtOAc, 6 hr swell, 10% NVP, degassed LDR, 0.05 Mrad. |
| PMMA/PVDF | a. 10% degassed NVP, LDR, 0.05 Mrad. |
| | b. 10% NVP, 5 hr swell, LDR, degassed, 0.15 Mrad. |
| | c. 2.5% EtOAc, 6 hr swell, 10% NVP, degassed, LDR, 0.05 Mrad. |
| PC/PP | a. 10% degassed NVP, LDR, 0.05 Mrad. |
| | b. 2.5% EtOAc, 6 hr swell, 10% NVP, LDR, degassed. |
| PC/PVDF | a. 10% degassed NVP, LDR, 0.05 Mrad. |
| | b. 10% NVP, 5 hr swell, LDR, degassed, 0.05 Mrad. |
| | c. 2.5% EtOAc, 6 hr swell, 10% NVP, degassed, LDR, 0.05 Mrad. |

*To produce C.A. less than about 25°.
**LDR : 30–300 rads/min.

We claim:

1. In a method for modifying a plastic surface of an article, said surface adapted for contact with living tissue of a human or non-human animal by the gamma-irradiation induced polymerized, chemically grafted coating thereon of a monomer comprising N-vinylpyrrolidone (NVP), 2-hydroxyethylmethacrylate (HEMA) or a mixture of (NVP) and (HEMA) so as to form a thin, hydrophilic coating of (1) poly-N-vinylpyrrolidone (PVP), (2) poly-2-hydroxyethylmethacrylate (PHEMA), or (3) a copolymer of NVP and HEMA [P(NVP-HEMA)] on said surface, the improvement comprising:
   conducting said gamma-irradiation induced graft polymerization in an aqueous solution under the following conditions:
   (1) monomer concentration in the range of from about 0.5% to about 50%, by weight;
   (2) total gamma dose in the range of from about 0.01 to less than about 0.50 Mrad;
   (3) gamma dose rate in the range of from about 10 to about 2500 rads/min; and
   (4) maintaining the molecular weight of the polymer in solution in the range of from about 250,000 to about 5,000,000.

2. The method of claim 1 further including one or more of the following conditions:
   (5) substantially excluding free oxygen from said graft polymerization solution;
   (6) maintaining the thickness of said polymer coating in the range of from about 100 Å to about 100 microns;

(7) including a free radical scavenger in said aqueous graft polymerization solution; and (8) including in said aqueous graft polymerization solution a swelling solvent for said PMMA surface.

3. The method of claim 1 wherein said article is a surgical instrument.

4. The method of claim 1 wherein said article is a medical device.

5. The method of claim 1 wherein said article is a prosthetic implant.

6. The method of claim 1 wherein said article is a soft or hard contact lens.

7. The method of claim 1 wherein said NVP, HEMA or mixture of NAP and HEMA is gamma-irradiation induced co-polymerized with an ionic monomer or mixture thereof under said conditions, the total monomer concentration in said solution being in the range of from about 1% to about 50%, by weight, and maintaining the molecular weight of the resultant copolymer in solution of NVP, HEMA or mixture of NVP and HEMA and said ionic monomer or mixture thereof in the range of from about 250,000 to about 5,000,000.

8. The method of claim 7 wherein said ionic monomer is a vinylsulfonic acid or a vinylcarboxylic acid.

9. The method of claim 8 wherein said vinylcarboxylic acid is acrylic, methacrylic or crotonic acid.

10. The method of claim 7 wherein said ionic monomer is an amino-functional monomer.

11. The method of claim 10 wherein said aminofunctional monomer is a vinylpyridine, an aminostyrene, an aminoacrylate or an aminomethacrylate.

12. An article prepared according to the method of claim 1.

13. An article according to claim 12 comprising a surgical instrument, medical device, prosthetic implant or contact lens.

* * * * *

UNITED STATES PATENT AND TRADEMARK OFFICE
CERTIFICATE OF CORRECTION

PATENT NO.   :   4,961,954

DATED        :   October 9, 1990

INVENTOR(S)  :   Eugene P. GOLDBERG, ET AL

It is certified that error appears in the above-identified patent and that said Letters Patent is hereby corrected as shown below:

In column 29, line 2 of claim 7: delete "NAP" and substitute therefor -- NVP --.

Signed and Sealed this

Eighth Day of September, 1992

Attest:

DOUGLAS B. COMER

*Attesting Officer*      *Acting Commissioner of Patents and Trademarks*